United States Patent [19]

Eszenyi et al.

[11] Patent Number: 5,703,113
[45] Date of Patent: Dec. 30, 1997

[54] BENZOPYRAN DERIVATIVES

[75] Inventors: Tibor Eszenyi, Tiszalök; Péter Sebök; László Frank, both of Tiszavasvári; Gyula Papp, Szeged; Tibor Timár, Tiszavasvári; Tamás Bartik, Veszprém, all of Hungary

[73] Assignee: Alkaloida Vegyeszeti Gyar, Tiszavasvari, Hungary

[21] Appl. No.: 481,440

[22] PCT Filed: Dec. 20, 1993

[86] PCT No.: PCT/HU93/00079

§ 371 Date: Nov. 8, 1995

§ 102(e) Date: Nov. 8, 1995

[87] PCT Pub. No.: WO94/14799

PCT Pub. Date: Jul. 7, 1994

[30] Foreign Application Priority Data

Dec. 19, 1992 [HU] Hungary ............ P 92 04049

[51] Int. Cl.$^6$ ............ A61K 31/40; A61K 31/35; C07D 407/04; C07D 309/10
[52] U.S. Cl. ............ 514/422; 514/456; 514/457; 548/525; 549/288; 549/289
[58] Field of Search ............ 548/525; 514/422, 514/456, 457; 549/288, 289

[56] References Cited

U.S. PATENT DOCUMENTS 5,043,344  8/1991  Englert et al. .................. 514/337

FOREIGN PATENT DOCUMENTS

| 0 076 075 | 4/1983 | European Pat. Off. . |
| 0 120 428 | 3/1984 | European Pat. Off. . |
| 0 107 423 | 5/1984 | European Pat. Off. . |
| 0 120 427 A1 | 10/1984 | European Pat. Off. . |
| 0 173 848 A2 | 3/1986 | European Pat. Off. . |
| 0 277 611 A2 | 8/1988 | European Pat. Off. . |
| 38 11 017 A1 | 10/1989 | Germany . |

*Primary Examiner*—Joseph McKane
*Attorney, Agent, or Firm*—Herbert Dubno; Jonathan Myers

[57] ABSTRACT

The invention relates to benzopyran compounds of formula (I) possessing pharmacological activity, as well as to pharmaceutical compositions containing the compounds of formula (I) and processes for the preparation thereof.

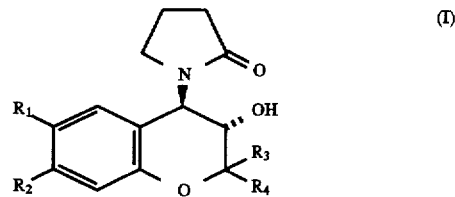

17 Claims, No Drawings

BENZOPYRAN DERIVATIVES

This application is a 371 of PCT/HU93/00079 filed Dec. 20, 1993.

FIELD OF THE INVENTION

The present invention relates to novel benzopyran derivatives of the formula

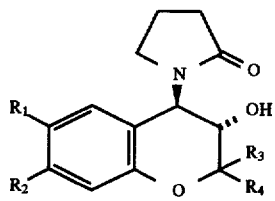

(I)

possessing pharmacological activity, as well as to pharmaceutical compositions containing the compounds of the formula (I). Further, the present invention relates to methods for preparing these compounds and the pharmaceutical compositions containing these compounds as well as novel intermediates.

BACKGROUND OF THE INVENTION

The preparation of certain compounds of the formula (I) having hypotensive effect by activating the potassium canal and pharmaceutically acceptable acid addition salts thereof is disclosed in European patent specifications Nos. 0,076,075, 0,093,535, 0,120,426, 0,120,427, 0,120,428, 0126,311 and 0,126,350. In the formula (I)

$R_1$ stands for a $(C_{1-4}$alkyl)carbonyl, $(C_{1-4}$alkoxy) carbonyl, nitro, formyl or cyano group or a halo atom, $R_2$ stands for a hydrogen atom, $R_3$ stands for a hydrogen atom or a $C_{1-4}$alkyl group, $R_4$ stands for a $C_{1-4}$alkyl group and the lactame ring is in trans position related to the hydroxy group.

The preparation of the compounds as disclosed in the literature is illustrated by reaction scheme No. 1:

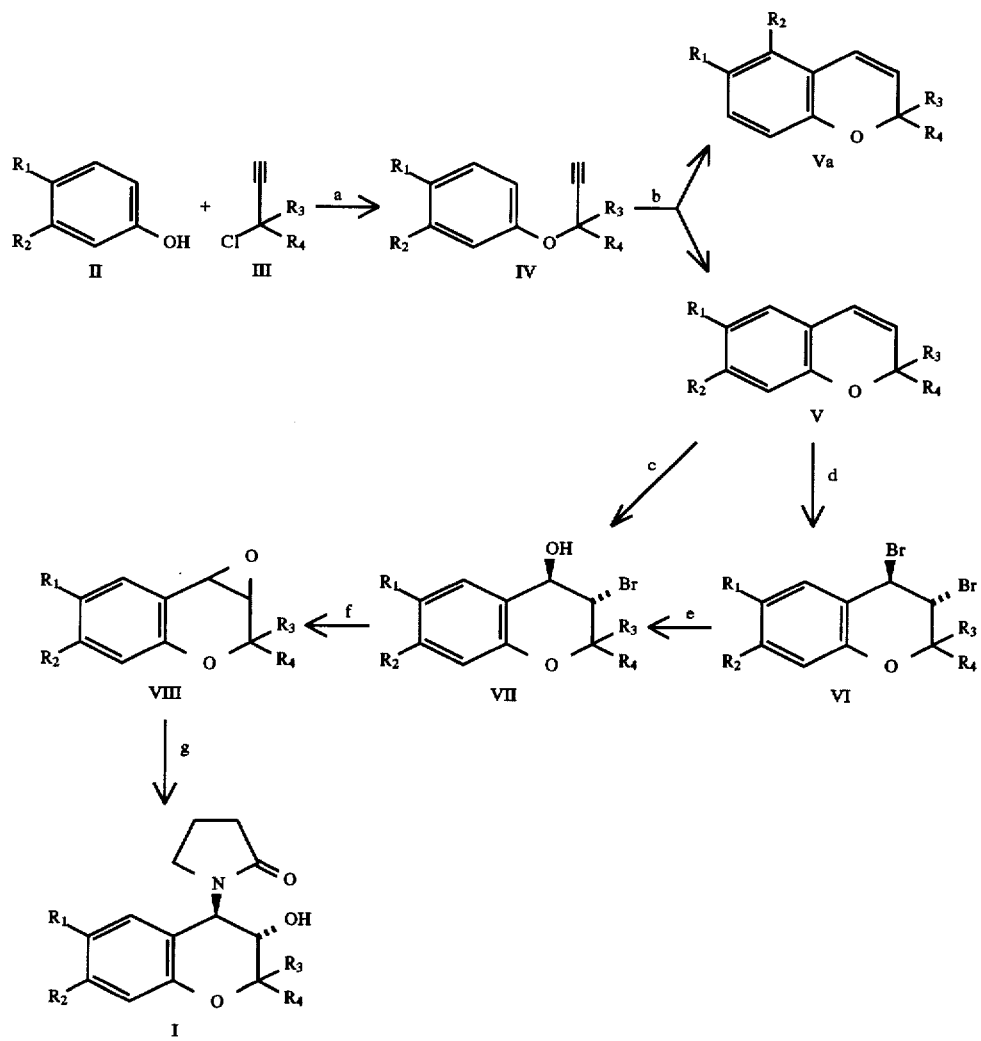

comprising reacting a suitably substituted phenol of the formula (II) with 3-chloro-1-propyne of the formula (III) resulting in an arylpropargyl ether of the formula (IV), a chromene of the formula (V) is then formed from the ether by thermic cyclization. Thereafter 3-bromo-4-chromanol of the formula (VII) may be formed from the chromene of the formula (V) either in one step by adding hypobromic acid, or in two steps, by hydrolyzing in aqueous acetone 3,4-dibromochromane of the formula (VI) obtained by adding elemental bromine to chromene of the formula (V). 3-Bromo-4-chromanol is converted into a 3,4-epoxy derivative of the formula (VIII) in an alkaline medium, compounds of the formula (I) are then prepared in a specific reaction.

The symbols in reaction scheme i stand for the following reaction conditions:

a: room temperature, a 40% sodium hydroxide solution, benzyl trimethyl ammonium hydroxide and methanol;

b: boiling under reflux in ortho dichlorobenzene;

c: N-bromosuccinimide, water and dimethyl sulfoxide;

d: bromine and carbon tetrachloride;

e: acetone and water;

f: sodium hydroxide, water and dioxane;

g: 2-pyrrolidone, sodium hydride and dimethyl sulfoxide.

If $R_2$ does not stand for hydrogen in the process described above, two substances are formed in reaction b as the ring formation may occur at two places. The formed disadvantageous regioisomer of the formula (Va) has to be separated from the reaction mixture which process is complicated and decreases the total yield.

In European patent specification No. 0,277,611 the preparation of such benzopyran derivatives of the formula (I) is disclosed in which $R_1$ stands for an arylsulfonyl or methylsulfonyl group, $R_2$ stands for a hydrogen atom, a hydroxy or $C_{1-2}$alkoxy group, $R_3$ is a hydrogen atom or a $C_{1-4}$alkyl group, $R_4$ is a $C_{1-4}$alkyl group and the lactame ring is in trans position related to the hydroxy group.

In the electrophilic substitution of 4-chromanone of the formula

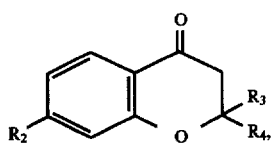

wherein $R_2$ stands for $C_{1-4}$alkoxy, $R_3$ and $R_4$ stand for $C_{1-4}$alkyl, a 4-chromanone of the formula

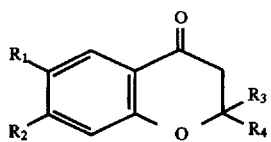

is obtained, the latter being reduced to 4- chromanol of the formula

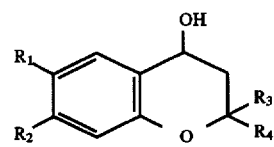

in a further reaction to obtain a chromene of the formula (V) in a water eliminating reaction. The derivative of the formula (I) is obtained from this compound through compounds of the formula (VII), then (VIII).

In the formulae $R_1$ stands for an arylsulfonyl or methylsulfonyl group, $R_2$ stands for a hydrogen atom, hydroxy or $C_{1-2}$alkoxy, $R_3$ is a hydrogen atom or a $C_{1-4}$alkyl group and $R_4$ is a $C_{1-4}$alkyl group and the lactame ring is in trans position related to the hydroxy group.

No process is known at the same time for the preparation of the compounds of the formula (I), wherein $R_1$ stands for a $C_{1-6}$alkyloxy, alkenyloxy, alkynyloxy, cycloalkoxy, aryloxy, aralkoxy, hydroxy, nitro, cyano, formyl, $C_{1-6}$acyl or cyano-$C_{1-6}$-alkyl group or halo, $R_2$ stands for a $C_{1-6}$alkoxy, alkenyloxy, alkynyloxy, cycloalkoxy, aryloxy, aralkoxy or hydroxy group, or $R_1$ and $R_2$ stand together for alkylenedioxy, and $R_3$ and $R_4$ stand together for a $C_{1-6}$alkyl group, The above compounds of the formula are novel.

According to literature data (J. Med. Chem. 1990, 33, 492) in compounds of the formula (I) for reaching hypotensive effect $R_1$ should represent a strong electron withdrawing substituent and $R_2$ generally a hydrogen atom.

We have, however, found that compounds of the formula (I) according the invention also possess a hypotensive effect. These compounds are characterized by being substituted together in positions 6 and 7, further, $R_1$ is not necessarily a strong electron withdrawing substituent and $R_2$ is not a hydrogen atom.

Further, we have found that benzopyrans of the formula (I) according to our invention also exert their effect by activating the potassium canal. Thus, these compounds may be useful according to David W. Robertson et al in the following fields of the therapy: a) hypertension; b) asthma; c) diseases of the urinary organs; d) heart failure, g) diseases of the central nervous system; and f) paralysis.

The invention provides processes for preparing the new compounds of the formula (I) through intermediates, the dominant part of which are also novel.

According to the invention compounds of the formula (I), wherein $R_1$ stands for a $C_{1-6}$alkoxy, alkenyloxy, alkynyloxy, cycloalkoxy, aryloxy, aralkoxy, hydroxy, nitro, cyano, formyl, $C_{1-6}$acyl or cyano-$C_{1-6}$-alkyl group or halo, $R_2$ stands for a $C_{1-6}$alkoxy, cycloalkoxy, aryloxy, aralkoxy group, or $R_1$ and $R_2$ together stand for alkylenedioxy, and $R_3$ and $R_4$ stand for a $C_{1-6}$alkyl group, with the provision that if $R_1$ is cyano or nitro, then $R_2$ cannot stand for methoxy or ethoxy, may be prepared by reducing a 4-chromanone of the formula (XVIII), wherein $R_1$ stands for a $C_{1-6}$alkoxy, alkenyloxy, alkynyloxy, cycloalkoxy, aryloxy, aralkoxy, hydroxy, nitro, cyano, formyl, $C_{1-6}$acyl or cyano-$C_{1-6}$-alkyl group or halo, $R_2$ stands for a $C_{1-6}$alkoxy, cycloalkoxy, aryloxy, aralkoxy group, $R_1$ and $R_2$ together stand for alkylenedioxy, and $R_3$ and $R_4$ stand for a $C_{1-6}$alkyl group, with metal hydrides, preferably sodium tetrahydroborate, in an amount of 1–5 equivalents, preferably 1.1 equivalents, in a polar or apolar solvent, preferably methanol and/or benzene, at a temperature of 0° to 100° C., preferably at 25° C., into a 4-chromanol derivative of the formula (XIX), boiling said 4-chromanol derivative of the formula (XIX) in a water immiscible solvent forming with it an azeotropic mixture, preferably in benzene, in the presence of a catalytic amount of p-toluene sulfonic acid for the preparation of 2H-chromene of the formula (V), converting said 2H-chromene of the formula (V) into a bromohydrine of the formula (VII) with N-bromosuccinimide in a dipolar aprotic solvent containing water as well, preferably in dimethyl sulfoxide, at a temperature of −10° to 50° C., preferably at 15° C., then reacting said bromohydrine derivative of the formula (VII) with 2-pyrrolidone in the presence of alkali metal alcoholates, preferably potassium tert-butoxide, at a temperature of 0° to 100° C., preferably at 25° C.

Compounds of the formula (I), wherein $R_1$ stands for a $C_{1-6}$alkoxy, cycloalkoxy, aryloxy, aralkoxy, hydroxy, nitro, cyano, formyl, $C_{1-6}$acyl or cyano-$C_{1-6}$-alkyl group or halo, $R_2$ stands for a hydroxy group and $R_3$ and $R_4$ stand for a $C_{1-6}$alkyl group, may be prepared hydrogenating compounds of the formula (I), wherein $R_1$ stands for a $C_{1-6}$alkoxy, cycloalkoxy, aryloxy, aralkoxy, hydroxy, nitro, cyano, formyl, $C_{1-6}$acyl or cyano-$C_{1-6}$-alkyl group or a halo atom, $R_2$ stands for an aralkoxy, preferably benzyloxy group and $R_3$ and $R_4$ stand for a $C_{1-6}$alkyl group, in a polar protic solvent, preferably methanol, in the presence of a catalyst, preferably palladium-on-charcoal catalyst, at a hydrogen pressure of 1 to 10 bar, preferably 5 bar.

Compounds of the formula (I), wherein $R_1$ stands for a $C_{1-6}$alkoxy alkenyloxy, alkynyloxy, cycloalkoxy, aryloxy, aralkoxy, hydroxy, nitro, cyano, formyl, $C_{1-6}$acyl or cyano-$C_{1-6}$-alkyl group or halo, $R_2$ stands for an alkenyloxy or alkynyloxy group and $R_3$ and $R_4$ stand for a $C_{1-6}$alkyl group, may be prepared by reacting a compound of the formula (I), wherein $R_1$ stands for a $C_{1-6}$alkoxy, alkenyloxy, alkynyloxy, cycloalkoxy, aryloxy, aralkoxy, hydroxy, nitro, cyano, formyl, $C_{1-6}$acyl or cyano-$C_{1-6}$alkyl group or halo, $R_2$ stands for a hydroxy group and $R_3$ and $R_4$ stand for a $C_{1-6}$alkyl group, with suitable alkenyl or alkynyl halogenides in a polar aprotic solvent, preferably acetone, in the presence of an acid binding agent, preferably potassium carbonate, and a catalytic amount of potassium iodide.

The invention also relates to the novel process by which 4-chromanone of the formula (XVIII) is prepared. Thus a) if in the formula (X) $R_1$ stands for a nitro group, $R_2$ is a $C_{1-4}$alkyloxy group, $R_3$ and $R_4$ stand together for a $C_{1-4}$dialkyl group, then a compound of the formula

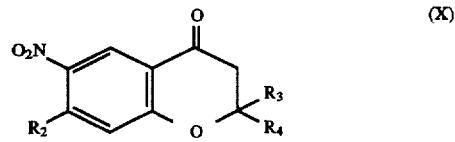

is obtained by nitrating a compound of the formula (IX), wherein $R_2$ is a $C_{1-4}$alkoxy group, $R_3$ and $R_4$ stand together for a $C_{1-4}$alkyl group (reaction scheme No. 2).

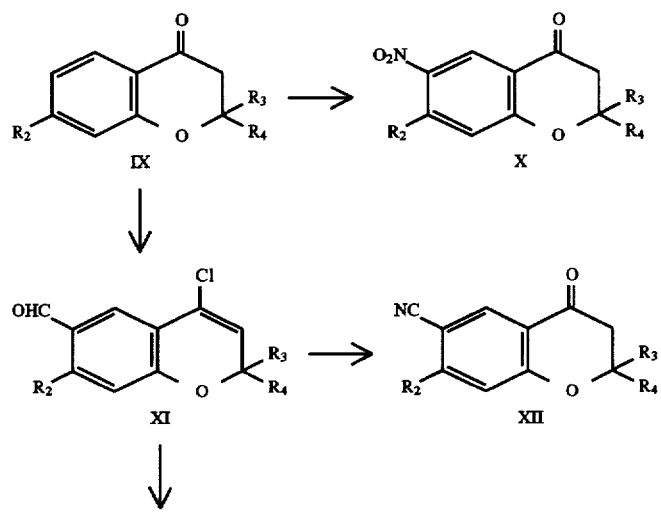

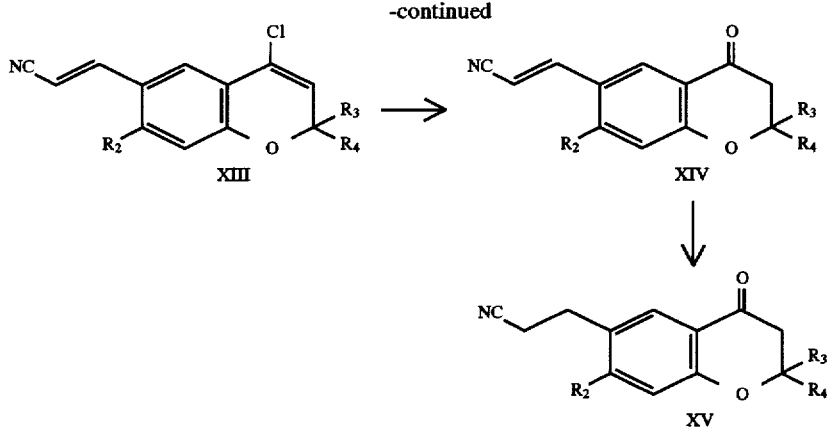

The nitration is performed with copper(II)nitrate in carboxylic anhydride, preferably acetic anhydride, at a temperature of 20°–100° C., preferably at 40° C. Compounds of the formula (X) are novel except when $R_2$ is $CH_3O$ (see Panayiotis Anastasis and Philip E. Brown: J- Chem. Soc. Perkin Trans. I., p. 2013–2018, 1982).

b) If in the formula (XII) $R_1$ stands for a cyano group, $R_2$ stands for a $C_{3-4}$alkoxy group, $R_3$ and $R_4$ together stand for a $C_{1-4}$alkyl group, then a compound of the formula (XII) is prepared from a formyl derivative of the formula (XI) by boiling same in 100% formic acid in the presence of hydroxylamine hydrochloric salt and alkali metal formiate. Said formyl derivative of the formula (XI) is obtained by subjecting a compound of the formula (IX), wherein $R_2$ stand for a $C_{1-4}$alkyloxy, $R_3$ and $R_4$ stand together for a $C_{1-5}$alkyl, to Vilsmeier formylation (reaction scheme 2). The preparation is performed by reacting a compound of the formula (IX), wherein $R_2$ stands for a $C_{3-4}$alkoxy group and $R_3$ and $R_4$ together stand for a $C_{1-4}$alkyl group, in a mixture of phosphorous trichloride oxide and dimethyl formamide at a temperature of 25°–100° C., preferably at 80° C., to obtain a derivative of the formula (XI), dissolving said compound of the formula (XI) in carboxylic acid and boiling the mixture preferably in formic acid, in the presence of an alkali metal formiate, preferably sodium formiate.

The compounds of the formula (XII) are novel.

c) If in the formula (XV) $R_1$ stands for a $C_{1-4}$alkyl-cyano group, $R_2$ stands for a $C_{1-4}$alkoxy group, $R_3$ and $R_4$ together stand for a $C_{1-4}$alkyl group, then 4-chromanone of the formula (XV), wherein $R_2$ stands for a $C_{1-4}$alkoxy group, $R_3$ and $R_4$ together stand for a $C_{1-4}$alkyl group, is prepared as follows: a compound of the formula (XI) and acetonitrile are condensed to obtain a compound of the formula (XIII). This compound is converted into a compound of the formula (XIV) by adding water to obtain a compound of the formula (XV) by catalytic hydrogenation (reaction scheme 2). The synthesis is carried out by condensing a compound of the formula (XI),
wherein
$R_2$ stands for a $C_{1-4}$alkoxy group and
$R_3$ and $R_4$ stand together for a $C_{1-4}$alkyl group, with acetonitrile in the presence of an alkali metal alcoholate, preferably potassium tert-butoxide, at a temperature of 0° to 100° C., preferably at 25° C., to obtain compounds of the formula (XIII), reacting said compounds of the formula (XIII) at a temperature of 0° to 100° C., preferably at 25° C. in the presence of a mineral acid, preferably 70% perchloric acid, to obtain a compound of the formula (XIV), then hydrogenating said compound of the formula (XIV) in a polar protic solvent, preferably methanol, in the presence of .a catalyst, preferably palladium-on-charcoal catalyst, at a hydrogen pressure of 1 to 10 bar, preferably at 5 bar. Compounds of the formula (XV) are novel.

d) If in general the formula (XVIII) $R_1$ stands for a hydrogen atom, $R_2$ stands for a hydroxy group, $R_3$ and $R_4$ together stand for a $C_{2-6}$alkyl group, then 4-chromanone of the formula (XVIII) is obtained by condensing resacetophenone of the formula

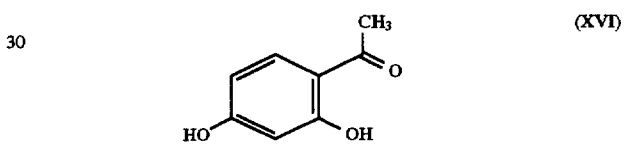

and a dialkyl ketone of the formula

in which formulae $R_3$ and $R_4$ together stand for a $C_{2-6}$ alkyl group (reaction scheme 3).

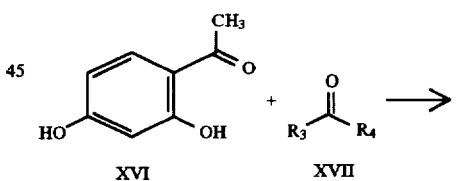

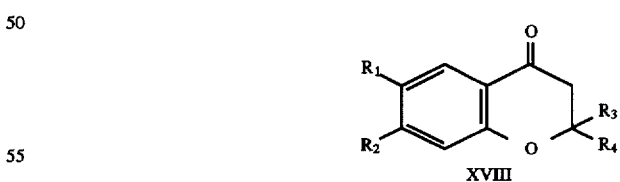

The reaction is performed by reacting a resacetophenone of the formula (XVI) with dialkyl ketone of the formula (XVII), wherein $R_3$ and $R_4$ stand for $C_{2-6}$alkyl, at a temperature of 0° to 100° C., preferably at 25° C., in the presence of a cyclic secondary amine, preferably pyrrolidine, in a water-immiscible solvent forming with same an azeotropic mixture, preferably toluene. Compounds of the formula (XVIII) are novel.

The invention also relates to the synthesis of the compounds of the formula (I) starting from 4-chromanone of the formula (XVIII), by converting same into chromene of the formula (V) through 4-chromanone of the formula (XIX). The chromene of the formula (V) is converted into a 3-bromo-4-chromanol of the formula (VII), from which a compound of the formula (I) is prepared through a 3,4-epoxy derivative of the formula (VIII) without isolating same (reaction scheme 4).

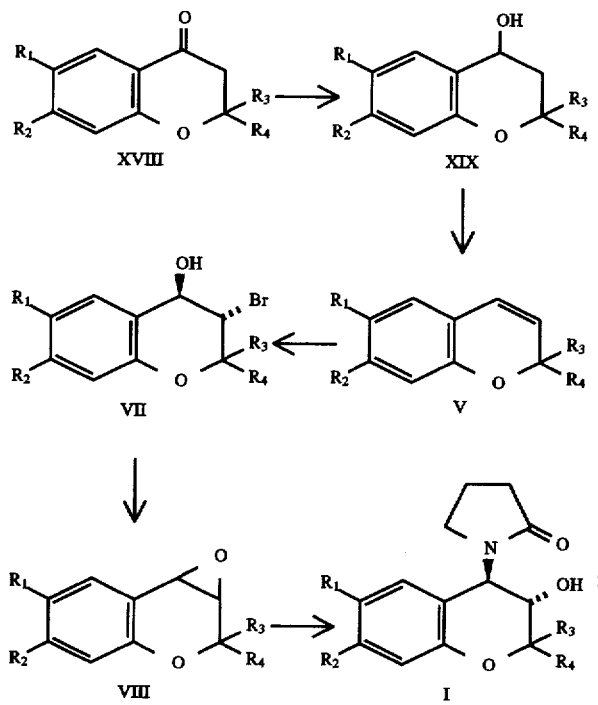

The potassium canal activating type compounds of the formula (I) show hypotensive activity, and can be used in the treatment of hypertension. Accordingly, the present invention also relates to pharmaceutical compositions containing as active ingredient a compound of the formula (I) in an effective amount together with pharmaceutically acceptable carriers, as well as to the preparation of said pharmaceutical compositions.

The pharmaceutical compositions according to the invention are prepared by using usual formulating auxiliaries. The formulation is carried out by methods generally used in the preparation of the known hypotensive agents.

Chemical examples

The process according to the invention is illustrated by the following non-limiting examples.

EXAMPLE 1

Preparation of (+/−)-6,7-dimethoxy-3,4-dihydro-2,2-dimethyl -trans-4-(2-oxo-1-pyrrolidinyl)-2H-benzo (b)pyran-3-ol 2.20 g (10 mmoles) of 6,7-dimethoxy-2,2-dimethyl-2H-chromene [prepared according to T. Timár and J. Cs. J ászberényi in J. Her. Chem. 25, 871 (1988)] are dissolved in 20 ml of dimethyl sulfoxide. The dimethyl sulfoxide contains 0.40 ml of water as well. Then 1.78 g (10 mmoles) of N-bromo-succinimide are added in small portions under vigorous stirring and cooling with ice. The reaction mixture is stirred at room temperature for 1 hour and poured onto 200 g of ice. The precipitated white crystalline substance is filtered off, washed with water and dried. It is pulped with hexane to obtain 2.93 g of 6,7-dimethoxy-trans-3-bromo-3,4-dihydro-2,2-dimethyl-2H-benzo (b) pyran-4-ol.

M.p.: 134°–135° C.

NMR (CDCl$_3$): 1.41 (3H, 1.57 (3H), 2.47 (1H, changeable), 4.12 (1H, d, J=10), 4.86 (1H, m), 6.35 (1H), 6.93 (1H).

2.85 g (9 mmoles) of bromohydrine derivative thus obtained are dissolved in 15 ml of 2-pyrrolidone and 2.01 g (18 mmoles) of potassium tert-butoxide are added thereto portionwise under vigorous stirring and cooling. The reaction mixture is stirred for another 2 hours at room temperature. 100 ml of water are added thereto and the product obtained is extracted with chloroform. The organic phase is washed neutral with water and dried on sodium sulfate to obtain the title product in a yield of 2.08 g.

M.p.: 171°–172° C.

NMR (CDCl$_3$): 1.25 (3H), 1.48 (3H), 2.07 (2H, m), 2.57 (2H, m), 3.22 (3H, 1 changeable H, broad m), 3.72 (1H, d, J=10), 3.77 (3H), 3.83 (3H), 5.22 (1H, d, J=10), 6.38 (1H), 6.40 (1H).

EXAMPLE 2

Preparation of (+/−)-6-methoxy-7-ethoxy-3,4-dihydro-2,2-dimethyl-trans-4-(2-oxo-1-pyrrolidinyl)-2H-benzo(b)pyran-3-ol The process as described in Example 1 is followed.

M.p.: 157°–158° C.

NMR (CDCl$_3$): 1.26 (3H), 1.45 (3H, t, J=6), 1.49 (3H), 2.07 (2H, m), 2.58 (2H, m), 3.20 (3H, 1 changeable H, broad m), 3.72 (1H, d, J=10), 3.78 (3H), 4.03 (2H, m), 5.21 (1H, d, J=10), 6.38 (2H).

EXAMPLE 3

Preparation of (+/−)-6-ethoxy-7-methoxy-3,4-dihydro-2,2-dimethyl-trans-4-(2-oxo-1-pyrrolidinyl)-2H-benzo (b) pyran-3-ol The process as described in Example i is followed.

M.p.: 164°–165° C.

NMR (CDCl$_3$): 1.27 (3H), 1.42 (3H, t, J=6), 1.50 (3H), 2.08 (2H, m), 2.58 (2H, m), 3.21 (3H, 1 changeable H, m), 3.74 (1H, d, J=10), 3.83 (3H), 3.97 (2H, m), 5.21 (1H, d, J=10), 6.40 (1H), 6.42 (1H).

EXAMPLE 4

Preparation of (+/−)-6-methoxy-7-benzyloxy-3,4-dihydro-2,2-dimethyl-trans-4-(2-oxo-1-pyrrolidinyl)-2H-benzo (b) pyran-3-ol The process as described in Example 1 is followed.

M.p.: 211°–212.5° C.

NMR (CDCl$_3$): 1.25 (3H), 1.47 (3H), 2.07 (2H, m), 2.57 (2H, m), 3.18 (3H, 1 changeable H, m), 3.72 (1H, m), 3.80 (3H), 5.07 (2H), 5.21 (1H, d, J=10), 6.42 (2H), 7.38 (5H, m).

EXAMPLE 5

Preparation of (+/−)-6-methoxy-7-hydroxy-3,4-dihydro-2,2-dimethyl-trans-4-(2-oxo-1-pyrrolidinyl)-2H-benzo (b) pyran-3-ol 0.39 g (1 mmole) of the 6-methoxy-7-benzyloxy derivative prepared as described in Example 4 are dissolved in 20 ml of methanol. 0.1 g of 10% palladium on charcoal catalyst is added thereto and the reaction mixture is hydrogenated at a hydrogen pressure of 5.0 bar under stirring. The reaction time is 6 hours. The catalyst is filtered off and the solution is evaporated. The oily product is dissolved in 50 ml of chloroform and washed with water. The phases are separated, dried over sodium sulfate and evaporated to obtain the title product in a yield of 0.25 g.

M.p.: 260° C. (decomposition).

NMR (CDCl$_3$): 1.25 (3H), 1.47 (3H), 2.07 (2H, m), 2.58 (2H, m), 3.23 (3H, 1 changeable H, m), 3.74 (1H, m), 3.81 (3H), 5.21 (1H, d, J=10), 5.65 (1H, changeable), 6.36 (1H), 6.43 (1H).

EXAMPLE 6

Preparation of (+/−)-6,7-dibenzyloxy-3,4-dihydro-2, 2-dimethyl-trans-4-(2-oxo-1-pyrrolidinyl)-2H-benzo (b) pyran-3-ol The process as described in Example i is followed.

M.p.: 162°–163° C.

NMR (CDCl$_3$): 1.23 (3H), 1.46 (3H), 1.67 (1H, m), 1.91 (1H), m), 2.42 (2H, m), 2.71 (1H, m), 3.02 (2H, m), 3.63 (1H, m), 5.12 (5H, m), 6.32 (1H), 6.46 (1H), 7.35 (10H).

EXAMPLE 7

Preparation of (+/−)-6,7-dihydroxy-3,4-dihydro-2,2-dimethyl-trans-4-(2-oxo-1-pyrrolidinyl)-2H-benzo (b)pyran-3-ol A 6,7-dibenzyloxy derivative prepared as described in Example 6 is hydrogenated as described in Example 5. The reaction time is 10 hours.

M.p.: decomposition.

NMR (CDCl$_3$): 1.26 (3H), 1.48 (3H), 2.07 (2H, m), 2.57 (2H, m), 3.23 (3H, 1 changeable H, m), 3.75 (1H, m), 5.22 (1H, d, J=10), 5.70 (2H, broad, changeable), 6.33 (1H), 6.46 (1H).

EXAMPLE 8

Preparation of (+/−)-6,7-methylenedioxy-3,4-dihydro-2,2-dimethyl-trans-4-(2-oxo-1-pyrrolidinyl)-2H-benzo (b) pyran-3-ol The process as described in Example i is followed.

M.p.: 161°–162° C.

NMR (CDCl$_3$): 1.25 (3H), 1.48 (3H), 2.08 (2H, m), 2.60 (2H, m), 3.22 (3H, 1 changeable H, m), 3.72 (1H, d, J=10), 5.15 (1H, d, J=10), 5.90 (2H, m), 6.35 (2H).

EXAMPLE 9

Preparation of (+/−) 16-bromo-7-methoxy-3,4-dihydro-2,2-dimethyl -trans-4-(2-oxo-1-pyrrolidinyl) -2H-benzo (b) pyran-3-ol 1.9 g (10 mmoles) of 7-methoxy-2,2-dimethyl-2H-chromene are dissolved in 20 ml of dimethyl-sulfoxide containing 0.40 ml of water, too. 3.56 g (20 mmoles) of N-bromo-succinimide are added thereto portionwise under vigorous stirring and external cooling with icy water. The reaction mixture is stirred at room temperature then poured onto 200 g of crushed ice. The precipitated white crystalline substance is filtered off, washed with water and dried. The product is pulped with hexane to obtain 3.09 g of 6-bromo-7-methoxy-trans-3-bromo-3,4-dihydro-2,2-dimethyl-2H-benzo (b) pyran-4-ol.

M.p.: 58°–59° C.

NMR (CDCl$_3$): 1.42 (3H), 1.61 (3H), 2.70 (1H, changeable), 3.68 (3H), 4.08 (1H, d, J=10), 4.85 (1H, d, J=10), 6.35 (1H), 7.62 (1H).

2.92 g (8 mmoles) of the bromohydrine derivative thus obtained are dissolved in 20 ml of 2-pyrrolidone, then 1.78 g (16 mmoles) of potassium tert-butoxide are added thereto under vigorous stirring and external cooling with icy water. The reaction mixture is stirred at room temperature for 4 hours, 100 ml of water are added thereto and the product is extracted with chloroform. The phase containing the chloroform is washed neutral with water, dried over sodium sulfate and evaporated to obtain the title product in a yield of 2.39 g.

M.p.: 165°–166° C.

NMR (CDCl$_3$): 1.27 (3H), 1.52 (3H), 2.13 (2H, m), 2.70 (2H, m), 3.25 (3H, 1 changeable H, m), 3.76 (1H, d, J=10), 3.86 (3H), 5.22 (1H, d, J=10), 6.41 (1H), 7.05 (1H).

EXAMPLE 10

Preparation of (+/−)-6-chloro-7-methoxy-3,4-dihydro-2,2-dimethyl-trans-4-(2-oxo-1-pyrrolidinyl)-2H-benzo (b) pyran-3-ol Starting from 6-chloro-7-methoxy-2,2-dimethyl -2H-chromene [prepared according to P. Sebók et al in Acta Chim. Hung 126 (4), 471 (1989)] one proceeds as described in Example 1.

M.p.: 196°–197.5° C.

NMR (CDCl$_3$): 1.27 (3H), 1.51 (3H), 2.10 (2H, m), 2.58 (2H, m), 3.16 (3H, 1 changeable H, m), 3.72 (1H, m), 3.85 (3H), 5.21 (1H, d, J=10), 6.42 (1H), 6.88 (1H).

EXAMPLE 11

Preparation of (+/−)-6-nitro-7-methoxy-3,4-dihydro-2,2-dimethyl-trans-4-(2-oxo-1-pyrrolidinyl -2H-benzo(b)pyran-3-ol 2.06 g (10 mmoles) of 7-methoxy-2,2-dimethyl-4-chromanone are dissolved in 12.5 ml of acetic anhydride. 3.02 g (12.5 mmoles) of Cu(NO$_3$)$_2$*3H$_2$O are added thereto in small portions under vigorous stirring while the temperature rises to 70° C. Then the mixture is stirred at 40° C. for 1.5 hours and poured onto 200 g of crushed ice. 1.88 g of yellowish crystalline 6-nitro-7-methoxy-2,2-dimethyl-4-chromanone are obtained, which is recrystallized in ethanol.

M.p.: 259°–261° C.

NMR (CDCl$_3$): 1.50 (6H), 2.72 (2H), 3.97 (3H), 6.52 (1H), 8.51 (1H).

1.75 g (7 mmoles) of 6-nitro-7-methoxy-2,2-dimethyl-4-chromanone are dissolved in 30 ml of methanol. 0.53 g (14 mmoles) of sodium boron hydride are added under vigorous stirring, the mixture is stirred at room temperature for 1 hour, the methanol is distilled off in vacuo, 100 ml of dichloromethane are added thereto and it is washed neutral with water. The organic phase is dried on sodium sulfate, dried and evaporated. 50 ml of benzene and 0.1 g of paratoluol sulfonic acid are added and boiled under reflux for 1 hour. The cooled solution is washed with water, dried over sodium sulfate and the benzene is distilled off in vacuo to obtain 1.48 g of 6-nitro-7-methoxy-2,2-dimethyl-2H-chromane.

M.p.: 79°–80° C.

NMR (CDCl$_3$): 1.46 (6H), 3.92 (3H), 5.60 (1H, d, J=10), 6.27 (1H, d, J=10), 6.43 (1H), 7.70 (1H).

1.41 g (6 mmoles) of 6-nitro-7-methoxy-2,2-dimethyl-2H-chromene are dissolved in 15 ml of dimethyl sulfoxide containing 0.3 ml of water. 1.06 g (6 mmoles) of N-bromosuccinimide are added under vigorous stirring and external cooling with ice. The reaction mixture is stirred at room temperature for 1.5 hours and poured onto 200 g of crushed ice. The precipitated white crystalline substance is filtered off, washed with water and dried to obtain 1.85 g of 6-nitro-7-methoxy-trans-3-bromo-3,4-dihydro-2,2-dimethyl-2H-benzo (b)pyran-4-ol.

M.p.: 143°–145° C.

NMR (CDCl$_3$): 1.45 (3H), 1.63 (3H), 2.72 (1H, broad, changeable), 3.90 (3H), 4.08 (1H, d, J=9.5), 4.87 (1H, d, J=9.5), 6.44 (1H), 8.19 (1H).

1.82 g (5.5 mmoles) of the bromohydride derivative thus obtained are dissolved in 15 ml of 2-pyrrolidone, then 1.23 g (11 mmoles) of 1.23 g of potassium tert-butoxide are added portionwise under vigorous stirring and external cooling with icy water. The reaction mixture is stirred at room temperature for 2 hours, 100 ml of water are added and the product is extracted with chloroform. The organic phase is washed neutral with water, washed, dried over sodium hydride and evaporated to obtain the title product in a yield of 1.50 g.

M.p.: 255°–257° C.

NMR (CDCl$_3$): 1.20 (3H), 1.44 (3H), 1.93 (2H, m), 2.37 (2H, m), 2.92 (2H, m), 3.67 (1H, dd, J$_1$=10, J$_2$=6), 3.83 (3H), 4.90 (1H, d, J$_1$=10), 5.73 (1H, d, J$_2$=6, changeable), 6.69 (1H), 7.43 (1H).

EXAMPLE 12

Preparation of (+/−)-6-nitro-7-ethoxy-3,4-dihydro-2,2-dimethyl-trans-4-(2-oxo-1-pyrrolidinyl)-2H-benzo (b)pyran-3-ol The process as described in Example 11 is followed.

M.p.: 225.5°–226.5° C.

NMR (CDCl$_3$): 1.31 (3H), 1.47 (3H, t, J=6), 1.53 (3H), 2.12 (2H, m), 2.70 (2H, m), 3.10. (1H, m), 3.33 (1H, m), 3.73 (1H, m), 3.93 (1H, m, changeable), 4.11 (2H, m), 5.22 (1H, d, J=10), 6.45 (1H), 7.58 (1H).

EXAMPLE 13

Preparation of (+/−)-6-nitro-7-n-propoxy-3,4-dihydro-2,2-dimethyl-trans-4-(2-oxo-1-pyrrolidinyl)-2H-benzo(b)pyran-3-ol The process as described in Example 11 followed.

M.p.: 207.5°–209.5° C.

NMR (CDCl$_3$): 1.07 (3H, t, J=6), 1.30 (3H), 1.53 (3H), 1.86 (2H, m), 2.11 (2H, m), 2.57 (2H, m), 3.22 (3H, 1 changeable H, m), 3.74 (1H, m), 4.00 (2H, m), 5.25 (1H, d, J=10), 6.45 (1H), 7.59 (1H).

EXAMPLE 14

Preparation of (+/−)-6-nitro-7-isopropoxy-3,4-dihydro-2,2-dimethyl-trans-4-(2-oxo-1-pyrrolidinyl)-2H-benzo (b) pyran-3-ol The process as described in Example 11 is followed.

M.p.: 221.5°–222.5° C.

NMR (CDCl$_3$): 1.31 (3H), 1.38 (6H), 1.52 (3H), 2.07 (2H, m), 2.56 (2H, m), 3.12 (1H, m), 3.35 (1H, m), 3.72 (1H, dd, J$_1$=6, J$_2$=10), 4.09 (1H, d, changeable, J$_1$=6), 1H, m), 5.21 (1H, d, J$_2$=10), 6.45 (1H), 7.53 (1H).

EXAMPLE 15

Preparation of (+/−)-6-cyano-7-methoxy-3,4-dihydro -2,2-dimethyl-trans-4-(2-oxo-1-pyrrolidinyl) -2H-benzo (b) pyran-3-ol 4.50 g (17.8 mmoles) of 6-formyl-4-chloro-7-methoxy-2,2-dimethyl-2H-chromene [prepared according to the method of P. Brown et al, J. Chem. Soc. Perkin Trans. (I), 1127 (1985) and T. Eszenyi and T. Timár, Synth. Comm., 20 (1990) 3219] are suspended in 40 ml of 100% of formic acid, 1.50 g (21 mmoles) of hydroxyl ammonium chloride and 2.50 g (24 mmoles) of sodium carbonate or an equivalent amount of sodium formiate are added. The reaction mixture is boiled under reflux for 3 hours, then poured onto 200 g of crushed ice. The separated beige precipitate is filtered off, washed with water and dried to obtain the below mentioned product in a yield of 3.89 g.

M.p.: 116°–118° C.

NMR (CDCl$_3$): 1.50 (6H), 2.72 (2H), 3.95 (3H), 6.45 (1H), 8.15 (1H).

4.0 g (17.3 Moles) of 6-cyano-7-methoxy-2,2-dimethyl-4-chromanone and 0.72 g (19 mmoles) of sodium boron hydride are suspended in 40 ml of benzene, then 10 ml of methanol are added dropwise while heated to reflux temperature. After a reaction time of half an hour the reaction mixture is cooled to 5°–10° C., the precipitate is filtered off and the benzene solution is evaporated. The evaporation residue is again dissolved in 20 ml of benzene, 0.4 g of para-toluene sulfonic acid are weighed in and the reaction mixture is boiled under reflux. Then it is cooled down, washed with water, dried on sodium sulfate and evaporated to obtain 3.12 g of a white crystalline substance.

M.p.: 92°–94° C.

NMR (CDCl$_3$): 1.45 (6H), 3.90 (3H), 5.57 (1H, d, J=10), 6.25 (1H, d, J=10), 6.40 (1H), 7.15 (1H).

2.15 g (10 mmoles) of 6-cyano-7-methoxy-2,2-dimethyl-2H-chromene are dissolved in 20 ml of dimethyl sulfoxide containing also 0.4 ml of water. Then 1.78 g (10 mmoles) of N-bromo-succinimide are added under external cooling with water and the reaction mixture is allowed to react for 2 hours at room temperature. Then it is poured onto 200 g of ice, the separated white precipitate is filtered, washed with water and dried to obtain 2.55 g of 6-cyano-7-methoxy-3,4-dihydro-2,2-dimethyl-trans-3-bromo-4-hydroxy-2H-benzo-(b)pyran.

M.p.: 144°–146° C.

NMR (CDCl$_3$) :1.45 (3H), 1.65 (3H), 2.85 (1H, changeable), 3.88 (3H), 4.08 (1H, d, J=10), 4.88 (1H, d, J=10), 6.38 (1H), 7.73 (1H).

2.55 g (8.2 mmoles) of the bromohydrine derivative thus-obtained are dissolved in 8 ml of 2-pyrrolidone, then 1.99 g (17.2 mmoles) of 97% potassium tert-butoxide are added under external cooling with water. The reaction mixture is stirred for 4 hours at room temperature, poured onto 100 g of crushed ice, the white precipitate is filtered off, washed with icy water, dried and crystallized from butanol to obtain the title product in an amount of 1.81 g.

M.p.: 239°–241° C.

NMR (CDCl$_3$): 1.30 (3H), 1.55 (3H), 2.13 (2H, m), 2.58 (2H, t), 3.09–3.35 (2H, m), 3.73 (1H, d, J=10), 3.88 (3H), 5.20 (1H, d, J=10), 6.40 (1H), 7.13 (1H).

EXAMPLE 16

Preparation of (+/−)-6-cyano-7-ethoxy-3,4-dihydro-2,2-dimethyl-trans-4-(2-oxo-1-pyrrolidinyl)-2H-benzo (b) pyran-3-ol The process as described in Example 15 is followed.

M.p.: 227°–229° C.

NMR (CDCl₃): 1.30 (3H), 1.48 (3H, t), 1.53 (3H), 2.13 (2H, m), 2.63 (2H, t), 3.08 (1H, m), 3.40 (1H, m), 3.73 (1H, d, J=10), 4.10 (2H, m), 5.18 (1H, d, J=10), 6.38 (1H), 7.10 (1H).

EXAMPLE 17

Preparation of (+/−)-6-cyano-7-propoxy-3,4-dihydro-2,2-dimethyl-trans-4-(2-oxo-1-pyrrolidinyl)-2H-benzo (b) pyran-3-ol The process as described in Example 15 is followed.
M.p.: 211°–213° C.

NMR (CDCl₃): 1.05 (3H, t), 1.30 (3H), 1.55 (3H), 1.85 (2H, m), 2.13 (2H, m), 2.58 (2H, t), 3.0 (1H, m), 3.35 (1H, m), 3.70 (1H, d, J=10), 3.95 (2H), m), 5.20 (1H, d, J=10), 6.38 (1H), 7.10 (1H).

EXAMPLE 18

Preparation of (+/−)-6-cyano-7-(1-methylethoxy)-3,4-dihydro-2,2-dimethyl-trans-4-(2-oxo-1-pyrrolidinyl)-2H-benzo (b)-pyran-3-ol The process as described in Example 15 is followed.
M.p.: 213°–215° C.

NMR (CDCl₃): 1.30 (3H), 1.40 (6H, t), 1.55 (3H), 2.13 (2H, m), 2.58 (2H, t), 3.10 (1H, m), 3.35 (1H, m), 3.70 (1H, d, J=10), 4.55 (1H, m), 5.20 (1H, d, J=10), 6.38 (1H), 6.38 (1H), 7.10 (1H).

EXAMPLE 19

Preparation of (+/−)-6-cyano-7-(1-methylpropoxy)-3,4-dihydro-2,2-dimethyl-trans-4-(2-oxo-1-pyrrolidinyl) -2H-benzo-(b) pyran-3-ol The process as described in Example 15 is followed.
M.p.: 199°–210° C.

NMR (CDCl₃): 1.02 (3H, t), 1.32 (6H, m), 1.55 (3H), 1.72 (2H, m), 2.12 (2H, m), 2.57 (2H, t), 3.10 (1H, m), 3.32 (1H, m), 3.72 (2H, m), 4.30 (1H, m), 5.17 (1H, d, J=10), 6.35 (1H), 7.10 (1H).

EXAMPLE 20

Preparation of (+/−)-7-benzyloxy-6-cyano-3,4-dihydro -2,2-dimethyl-trans-4-(2-oxo-1-pyrrolidinyl) -2H-benzo (b) pyran-3-ol The process as described in Example 15 is followed.
M.p.: 233°–235° C.

NMR (CDCl₃): 1.28 (3H, s), 1.52 (3H, s), 2.12 (2H, m), 2.57 (2H, t), 3.07 (1H, m), 3.30 (2H, m), 3.70 (1H, m), 5.17 (3H, m), 6.45 (1H, s), 7.15 (1H, s).

EXAMPLE 21

Preparation of (+/−)-7-hydroxy-6-cyano-3,4-dihydro-2,2-dimethyl-trans-4-(2-oxo-1-pyrrolidinyl)-2H-benzo (b) pyran-3-ol Starting from a 6-cyano-7-benzyloxy derivative prepared according to Example 20, the process as described in Example 5 is followed.

M.p.: 280° C. (decomposition).

NMR (DMSO-d₆): 1.16 (3H, s), 1.40 (3H, s), 1.97 (2H, m), 2.38 (2H, m), 2.92 (1H, m), 3.30 (1H, m), 3.62 (1H, d, J=10), 4.85 (1H,d, J=10), 5.64 (1H, changeable H), 6.37 (1H, s), 7.06 (1H, s), 11.00 (1H, changeable H).

EXAMPLE 22

Preparation of (+/−)-7-allyloxy-6-cyano-3,4-dihydro-2,2-dimethyl-trans-4-(2-oxo-1-pyrrolidinyl)-2H-benzo (b) pyran-3-ol 0.30 g (1 mmole) of a compound according to Example 21 is reacted with 0.34 g (1.2 mmoles) of allylbromide in 15 ml of acetone for 4.5 hours at reflux temperature in the presence of 0.20 g of potassium carbonate and a catalytic amount of potassium iodie. The reaction mixture is cooled back, filtered off and evaporated and the rough product obtained is recrystallized from ethyl acetate.

M.p.: 204°–206° C.

NMR (CDCl₃): 1.28 (3H, s), 1.52 (3H, s), 2.10 (2H, m), 2.54 (2H, t), 3.05 (1H, m), 3.32 (1H, m), 3.72 (2H, m, 1 changeable H), 4.59 (2H, d, J=6), 5.18 (1H, d, J=10), 5.25–5.55 (2H, m), 5.90–6.15 (1H, m), 6.39 (1H, s), 7.12 (1H, s).

EXAMPLE 23

Preparation of (+/−)-6-formyl-7-methoxy-3,4-dihydro-2,2-dimethyl-trans-4-(2-oxo-1-pyrrolidinyl)-2H-benzo(b)pyran-3-ol Starting from 6-formyl-7-methoxy-2,2-dimethyl -2H-chromene [prepared according to the method of S. Yamaguchi et al in Bull. Chem. Sc. japan, 57, 442 (1984)] one proceeds as described in Example 15.

(+/−)-trans-3-bromo-3,4-dihydro-2,2-dimethyl -6-formyl-7-methoxy-2H-benzo (b) pyran-4-ol M.p.: 149°–151° C.

NMR (CDCl₃): 1.45 (3H, s), 1.65 (3H, s), 2.93 (1H, broad), 3.88 (3H, s), 4.10 (1H, d, J=10), 4.90 (1H, d, J=10U, 6.38 (1H, s), 8.03 (1H, s), 10.28 (1H, s).

(+/−)-6-Formyl-7-methoxy-3,4-dihydro-2,2-dimethyl-trans-4-(2-oxo-1-pyrrolidinyl)-2H-benzo (b)pyran-3-ol M.p.: 219°–221° C.

NMR (CDCl₃): 1.30 (3H, s), 1.55 (3H, s), 2.10 (2H, m), 2.55 (2H, m), 3.00–3.40 (2H, m), 3.60 (3.90 (5H, m), 5.22 (1H, d, J=10), 6.40 (1H, s), 7.45 (1H, s), 10.25 (1H, s).

EXAMPLE 24

Preparation of (+/−)-7-ethoxy-6-formyl-3,4-dihydro-2,2-dimethyl-trans-4-(2-oxo-1-pyrrolidinyl)-2H-benzo(b)pyran-3-ol The process as described in Example 21 is followed.
M.p.: 203°–206° C.

NMR (CDCl₃): 1.30 (3H, s), 1.45 (3H, t), 1.55 (3H, s), 2.10 (2H, m), 2.55 (2H, m), 3.00–3.40 (2H, m), 3.60–3.80 (2H, m), 4.08 (2H, q), 5.22 (1H, d, J=10), 6.38 (1H, s), 7.45 (1H, s), 10.30 (1H, s).

EXAMPLE 25

Preparation of (+/−)-6-formyl-7-propoxy-3,4-dihydro-2,2-dimethyl-trans-4-(2-oxo-1-pyrrolidinyl)-2H-benzo (b) pyran-3-ol The process as described in Example 21 is followed.
M.p.: 190°–192° C.

NMR (CDCl$_3$): 1.05 (3H, t), 1.30 (3H, s), 1.55 (3H, s), 1.85 (2H, m), 2.10 (2H, m), 2.55 (2H, m), 3.00–3.40 (2H, m), 3.60–3.80 (2H, m), 3.95 (2H, q), 5.22 (1H, d, J=10), 6.38 (1H, s), 7.45 (1H, s), 10.32 (1H, s).

EXAMPLE 26

Preparation of (+/−)-(3,4-dihydro-2,2-dimethyl -7-methoxy-trans-4-(2-oxo-1-pyrrolidinyl)-2H-benzo (b) pyran-3-ol-6-yl)-propane carbonitrile 5.00 g (19.8 mmoles) of 6-formyl-4-chloro -7-methoxy-2,2-dimethyl-2H-chromane are dissolved at room temperature in 100 ml of acetonitrile. Then 2.70 g (23.3 mmoles) of 97% potassium tert-butoxide are added and the reaction mixture is boiled under reflux for 1 hour. The reaction mixture is then evaporated and poured onto 200 g of crushed ice, extracted three time with 50 ml of chloroform each, the chloroformic solution is dried and evaporated to obtain 2-(2,2-dimethyl-4-chloro-7-methoxy-2H-chromene-6-yl)-trans-propene carbonitrile in the form of a yellow oil.

NMR (CDCl$_3$): 1.48 (6H, s), 3.85 (3H, s), 5.70 (1H, s), 5.95 (1H, d, J=17), 6.40 (1H, s), 7.42 (1H, :s), 7.55 (1H, d, J=17).

The 2-(2,2-dimethyl-4-chloro-7-methoxy-2H-chromene-6-yl)-trans-propene carbonitrile is dissolved in 25 ml of acetonitrile and 10 ml of 70% perchloric acid are added thereto. The reaction mixture is let to react at 40° C. for an hour. It is then cooled with ice, poured onto 200 g of crushed ice, extracted with chloroform, dried on sodium sulfate and evaporated. The evaporation residue is dissolved in 15 ml of methanol and cooled down to obtain 0.97 g of white crystalline trans-2-(2,2-dimethyl-7-methoxy -4-chromanone-6-yl)-propene carbonitrile.

M.p.: 127°–129° C.

NMR (CDCl$_3$): 1.48 (6H, s), 2.71 (2H, s), 3.93 (3H, s), 6.00 (1H, d, J=17), 6.42 (1H, s), 7.52 (1H, d, J=17), 7.95 (1H, s).

0.95 g (3.45 mmoles) of trans-2,2-dimethyl-7-methoxy-4-chromanone-6-yl)-propene carbonitrile are dissolved in 30 ml of acetone, 0.10 g of 10% palladium on charcoal catalyst are added thereto and the reaction mixture is reduced at a pressure of 5.0 bar for 4 hours. Then the catalyst is filtered off and the solution is evaporated to obtain white crystalline 6-β-cyanoethyl-7-methoxy-2,2-dimethyl-4-chromanone in a yield of 97%.

M.p.: 105°–107° C.

NMR (CDCl$_3$): 1.45 (6H, s), 2.60 (2H, t), 2.68 (2H, s), 2.90 (2H, s), 3.87 (3H, s), 6.38 (1H, s), 7.65 (1H, s).

Further one proceeds as described in Example 15 to obtain white crystalline (+/−)-(3,4-dihydro -2,2-dimethyl-7-methoxy-trans-4-(2-oxo-1-pyrrolidinyl)-2H-benzo (b) pyran-3-ol-6-yl)-propane carbonitrile.

M.p.: 180°–182° C.

NMR (CDCl$_3$): 1.18 (3H, s), 1.50 (3H, s), 2.08 (2H, m), 2.58 (4H, m), 2.65 (1H, m), 2.95 (1H, m), 3.23 (2H, m), 3.50 (1H, m), 3.70 (1H, m), 3.78 (3H, s), 5.20 (1H, d, J=10), 6.25 (1H, s), 6.25 (1H, s), 6.73 (1H, s).

EXAMPLE 27

Preparation of (+/−)-(3,4-dihydro-2,2-dimethyl -7-ethoxy-trans-4-(2-oxo-1-pyrrolidinyl)-2H-benzo (b) pyran-3-ol-6-yl)-propane carbonitrile The process as described in Example 25 is followed.
M.p.: 208°–210° C.

NMR (CDCl$_3$): 1.28 (3H, s), 1.40 (3H, t), 1.50 (3H, s), 2.08 (2H, m), 2.60 (5H, m), 3.68 (1H, m), 2.95 (1H, m), 3.25 (2H, m), 3.73 (2H, m), 4.00 (2H, q), 5.23 (1H, d, J=10), 6.35 (1H, s), 6.73 (1H, s).

EXAMPLE 28

Preparation of (+/−)-6-cyano-7-methoxy-3,4-dihydro -2,2-diethyl-trans-4-(2-oxo-1-pyrrolidinyl)-2H-benzo (b) pyran-3-ol 1.52 g (10.0 mmoles) of resacetophenone are dissolved in 1.20 g (14.0 mmoles) of diethyl ketone, then 1.42 g (20.0 mmoles) pyrrolidine [prepared according to the method of H. J. Kabbe in Synthesis, 886 (1978)] are added thereto. The reaction mixture is allowed to stand at room temperature for 24 hours, then 40 ml of toluene are added. The reaction mixture is boiled under reflux for 10 hours by using a water separator. Then it is cooled back, washed subsequently with 10% hydrochloric acid and water, thereafter it is dried and evaporated to obtain 1.41 g of 2,2-diethyl-7-hydroxy-4-chromanone in the form of a pale yellow viscous oil which crystallizes on standing.

M.p.: 97°–99° C.

NMR (CDCl$_3$): 0.92 (6H, t), 1.75 (4H, m), 2.68 (2H, s), 6.38 (1H, d, J=2), 6.50 (1H, dd, J$_1$=2, J$_2$=8.5), 7.78 (1H, d, J$_2$=8.5 ).

1.41 g (6.40 mmoles ) of 2,2-diethyl-7-hydroxy-4-chromanone thus obtained is methylated with methyl iodide according to the method of T. Tímír et al [Acta Chimica Hungarica, 125(2), 303 (1980)] to obtain 1.36 g of 2,2-diethyl-7-methoxy-4-chromanone in the form of a pale yellow oil.

NMR (CDCl$_3$): 0.95 (6H, t), 1.75 (4H, m), 2.75 (2H, s), 3.80 (3H, s), 6.40 (1H, d, J$_1$=2), 6.55 (1H, dd, J$_1$=2, J$_2$=8.5), 7.75 (1H, d, J$_2$=8.5).

Furtheron one proceeds as described in Example 15 to obtain 6-cyano-7-methoxy-3,4-dihydro-2,2-diethyl -trans-4-(2-oxo-1-pyrrolidinyl)-2H-benzo(b)pyran-3-ol in the form of a white crystalline substance.

M.p.: 193°–195° C.

NMR (CDCl$_3$): 0.90 (3H, t), 1.05 (3H, t), 1.60–2.20 (6H, multiplet), 2.55 (2H, m), 3.05 (1H, m), 3.30–3.60 (2H, multiplet), 3.70 (1H, d, J=10), 3.85 (3H, s), 3.90 (1H, m, changeable), 5.30 (1H, d, J=10), 6.42 (1H, s), 7.10 (1H, s).

EXAMPLE 29

Preparation of (+/−)-6-cyano-7-ethoxy-3,4-dihydro-2,2-diethyl-trans-4-(2-oxo-1-pyrrolidinyl)-2H-benzo (b) pyran-3-ol The process as described in Example 28 is followed.
M.p.: 187°–189° C.

NMR (CDCl$_3$): 0.90 (3H, t), 1.05 (3H, t), 1.45 (3H, t), 1.70–2.10 (6H, multiplet), 2.55 (2H, m), 3.05 (1H, m), 3.40 (1H, m), 3.95–4.10 (4H, multiplet), 5.30 (1H, d, J=10), 6.40 (1H, s), 7.10 (1H, s).

BIOLOGICAL EXAMPLES

1. Measuring the bandage to potassium canal and selectivity on isolated arteria mesenterica anterior of rabbits The measurements were carried out by adapting the methods of R. P. Hof et al (Circulation Research, 1988, 62, 679) and J. C. Clapham et al (J. Auton. Pharmac., 1987, 7, 233).

Rabbits of both sexes weighing 2000–2500 g were anesthetized by a hit at the nape, the abdominal wall was cut open and the arteria mesenterica anterior was mounted after exsanguination. The artery was put into a Krebs solution of a temperature of 37° C. infiltrated with carbogene while removing the interstitial residues. Then a 2 mm wide spiral is cut from the artery and this artery stripe is prestretched in an organ pot in Krebs solution of a temperature of 37° C., infiltrated with carbogene, by a stretching of 0.5 g.

In the experiment Hugo Basile type dynamometer heads, Hugo Basile type amplifiers and Perkin Elmer type potentiometer have been used for amplifying and fixing the signs.

Two parallel organs were used for the qualitative tests. One of them was contracted by adding 30 mmoles of KCl after an incubation time of 1 hour, the other one by 5 μmoles of adrenaline. Then the arteries were relaxed by the cumulative addition of the substance to be examined. The system was washed with a Krebs solution containing 30 mmoles of tetraethyl ammonium bromide (TEA) and the organs were incubated for 30 minutes in a TEA-containing medium. After incubation the organs were again contracted with potassium and noradrenaline and a dilatation was induced by using the substance to be examined. In a quantitative test organs contracted with 5 μmoles of noradrenaline were relaxed with the substance to be examined and the dose inducing a 50% dilatation was determined.

| Compound | pA$_2$ | Selectivity | Mechanism of effect |
|---|---|---|---|
| BRL 34915 | 6.64 ± 0.23 | selective | Potassium canal activator |
| Example 1 | 5.78 ± 0.24 | selective | Potassium canal activator |
| Example 9 | 6.08 ± 0.32 | selective | Potassium canal activator |
| Example 10 | 5.47 ± 0.60 | selective | Potassium canal activator |
| Example 11 | 5.65 ± 0.27 | selective | Potassium canal activator |
| Example 15 | 6.76 ± 0.23 | selective | Potassium canal activator |

The compounds according, to the other Examples have also been examined and found to be effective.

It has been recognized that the compounds of the formula (I) can be used for treating different types of hypertension such as essential hypertension or secondary hypertension (of renal or hormonal origin) or any other disease requiring the decrease of the blood pressure by an antihypertensive composition.

2. Decrease of blood pressure on normotensive rats measured by average arterial tension Wistar rats of both sexes weighing 230–260 g were used in the experiments. The rats were narcotised by 40 mg/kg of pentobarbital. The trachea was mounted and a polyethylene canula was introduced into the trachea, vena jugularis sinester and to the arteria carotis communis sinester. The substances to be examined were introduced into the organism of the animal through the duodenum. The pulsatory, systolic and diastolic blood pressure and the pulse were continuously measured by using a Statham type tensiometer head and haemodynamic measuring system produced by the Hungarian firm Experimetria Kft. After the blood pressure has become stable 0.75 μg of adrenaline were administered intravenously to measure the effect of alpha-adrenergic receptors on the blood pressure. After the hypertension has ceased 0.1 μg/kg of isoproterenole is added in order to characterize the activity of the β-adrenerg receptors. After tachycardia has ceased the test compound was administered i.d. and the treatment with the receptor stimulants was repeated after an hour in order to characterize the effect of the test compound on adrenergic receptor subclasses.

Change of the blood pressure on normotensive rats measured on six test animals

| Compound | Time (min) | Average arterial tension | Decrease | Pulse |
|---|---|---|---|---|
| BRL 34915 | 0 | 112 ± 9 | — | 368 ± 44 |
|  | 1 | 45 ± 2 | −67 | 368 ± 31 |
| in a dose | 10 | 45 ± 2 | −67 | 382 ± 25 |
| of 1 mg/kg | 30 | 49 ± 4 | −63 | 377 ± 19 |
|  | 60 | 61 ± 11 | −51 | 373 ± 12 |
| Example 1 | 0 | 107 ± 11 | — | 394 ± 27 |
|  | 1 | 56 ± 6 | −51 | 403 ± 34 |
| in a dose | 10 | 56 ± 6 | −51 | 400 ± 31 |
| of 1 mg/kg | 30 | 49 ± 4 | −45 | 400 ± 31 |
|  | 60 | 71 ± 20 | −36 | 382 ± 31 |
| Example 9 | 0 | 117 ± 19 | — | 406 ± 51 |
|  | 1 | 119 ± 16 | +2 | 406 ± 51 |
| in a dose | 10 | 58 ± 5 | −59 | 436 ± 62 |
| of 10 mg/kg | 30 | 65 ± 15 | −52 | 430 ± 63 |
|  | 60 | 87 ± 18 | −30 | 430 ± 63 |
| Example 10 | 0 | 108 ± 15 | — | 402 ± 4 |
|  | 1 | 62 ± 3 | −46 | 418 ± 18 |
| in a dose | 10 | 68 ± 6 | −40 | 436 ± 18 |
| of 5 mg/kg | 30 | 96 ± 15 | −12 | 424 ± 10 |
|  | 60 | 109 ± 26 | +1 | 396 ± 13 |
| Example 11 | 0 | 121 ± 21 | — | 388 ± 10 |
|  | 1 | 115 ± 11 | −6 | 373 ± 15 |
| in a dose | 10 | 97 ± 23 | −24 | 394 ± 20 |
| of 1 mg/kg | 30 | 105 ± 18 | −16 | 382 ± 18 |
|  | 60 | 107 ± 12 | −14 | 382 ± 18 |
| Example 15 | 0 | 125 ± 13 | — | 412 ± 45 |
|  | 1 | 92 ± 10 | −33 | 439 ± 42 |
| in a dose | 10 | 103 ± 5 | −22 | 430 ± 45 |
| of 1 mg/kg | 30 | 118 ± 15 | −7 | 430 ± 45 |
|  | 60 | 122 ± 10 | −3 | 412 ± 37 |

What we claim is:

1. A compound of the Formula (I)

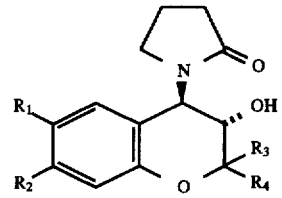

wherein $R_1$ is $C_1$ to $C_6$ alkoxy, alkenyloxy, alkynyloxy, cycloalkoxy, aryloxy, aralkoxy, hydroxy, nitro, cyano, formyl, $C_1$ to $C_6$ acyl, cyano-$C_1$–$C_6$alkyl or halo;

$R_2$ is $C_1$ to $C_6$ alkoxy, alkenyloxy, alkynyloxy, cycloalkoxy, aryloxy, aralkoxy or hydroxy; or $R_1$ and $R_2$ together are alkylenedioxy; and $R_3$ and $R_4$ are each $C_1$ to $C_6$ alkyl.

2. A compound of the Formula

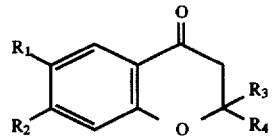

wherein $R_1$ is nitro, cyano or cyano-$C_1$–$C_6$alkyl;

$R_2$ is $C_1$ to $C_4$ alkoxy; and $R_3$ and $R_4$ are each $C_1$ to $C_4$ alkyl.

3. A compound of the Formula (I) defined in claim 1 and selected from the group consisting of:

(+/−)-6,7-dimethoxy-3,4-dihydro-2,2-dimethyl-trans-4-(2-oxo-1-pyrrolidinyl)-2H-benzo(b)pyran-3-ol;

(+/−)-6-bromo-7-methoxy-3,4-dihydro-2,2-dimethyl-trans-4-(2-oxo-1-pyrrolidinyl)-2H-benzo(b)pyran-3-ol;

(+/−)-6-chloro-7-methoxy-3,4-dihydro-2,2-dimethyl-trans-4-(2-oxo-1-pyrrolidinyl)-2H-benzo(b)pyran-3-ol;

(+/−)-6-nitro-7-methoxy-3,4-dihydro-2,2-dimethyl-trans-4-(2-oxo-1-pyrrolidinyl)-2H-benzo(b)pyran-3-ol; and (+/−)-6-cyano-7-methoxy-3,4-dihydro-2,2-dimethyl-trans-4-(2-oxo-1-pyrrolidinyl)-2H-benzo(b)pyran-3-ol.

4. An anti-hypertensive pharmaceutical composition which comprises a therapeutically effective amount of a compound of the Formula (I) defined in claim 1 in combination with a pharmaceutically acceptable inert carrier.

5. A method of treating hypertension in a mammalian subject which comprises the step of administering to said mammalian subject to be treated, a therapeutically effective amount of the compound of the Formula (I) defined in claim 1.

6. A process for the preparation of a compound of the Formula (I)

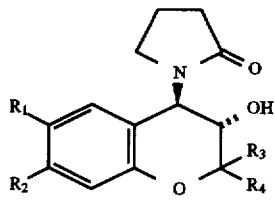

wherein $R_1$ is $C_1$ to $C_6$ alkoxy, alkenyloxy, alkynyloxy, cycloalkoxy, aryloxy, aralkoxy, hydroxy, nitro, cyano, formyl, $C_1$ to $C_6$ acyl, cyano-$C_1$-$C_6$alkyl or halo;

$R_2$ is $C_1$ to $C_6$ alkoxy, alkenyloxy, alkynyloxy, cycloalkoxy, aryloxy, aralkoxy or hydroxy; or $R_1$ and $R_2$ together are alkylenedioxy; and $R_3$ and $R_4$ are each $C_1$ to $C_6$ alkyl, which comprises the steps of:

(a) reducing a compound of the Formula (XVIII)

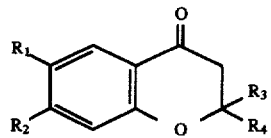

with a metal hydride to yield a compound of the Formula (XIX)

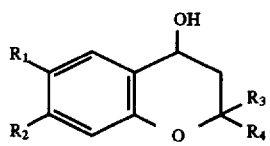

(b) dehydrating the compound of the Formula (XIX) by boiling said compound in a water immiscible solvent forming therewith an azeotropic mixture in the presence of a catalytically effective amount of p-toluene sulfonic acid to obtain a compound of the Formula (V)

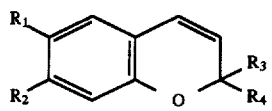

(c) converting the compound of the Formula (V) with N-bromo-succinimide to a compound of the Formula (VII)

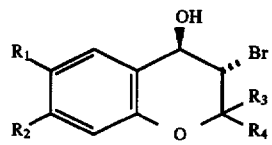

and (d) reacting the compound of the Formula (VII) with 2-pyrrolidone in the presence of an alkali metal alcoholate to obtain the compound of the Formula (I).

7. The process for preparing a compound of the Formula (I) defined in claim 6 wherein $R_2$ is hydroxy further comprising the step of catalytically hydrogenating under pressure a compound of the Formula (I) where $R_2$ is aralkoxy.

8. The process for preparing a compound of the Formula (I) defined in claim 6 wherein $R_2$ is alkenyloxy or alkynyloxy further comprising the step of reacting a compound of the Formula (I) where $R_2$ is hydroxy with an alkenyl or alkynyl halogenide in the presence of an acid binding agent and a catalytic amount of potassium iodide.

9. The process for preparing a compound of the Formula (I) defined in claim 6 wherein according to step (a) the metal hydride is sodium borohydride.

10. The process for preparing a compound of the Formula (I) defined in claim 6 wherein according to step (d) the alkali metal alcoholate is potassium tert-butoxide.

11. The process for preparing a compound of the Formula (I) defined in claim 7 wherein $R_2$ is hydroxy in that the catalyst is palladium-on-charcoal.

12. The process for preparing a compound of the Formula (I) defined in claim 8 wherein $R_2$ is alkenyloxy or alkynyloxy in that the acid binding agent is potassium carbonate.

13. A process for preparing a compound of the Formula (X)

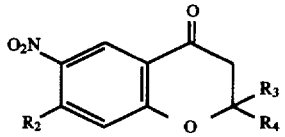

wherein $R_2$ is $C_1$ to $C_4$ alkoxy; and $R_3$ and $R_4$ are each $C_1$ to $C_4$ alkyl, which comprises the step of nitrating a compound of the Formula (IX)

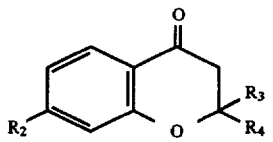

with copper(II)nitrate in a carboxylic anhydride.

14. A process for the preparation of a compound of the Formula (XII)

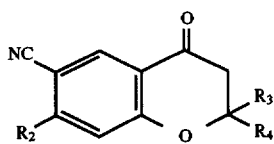

wherein

R₂ is $C_1$ to $C_4$ alkoxy; and

R₃ and R₄ are each $C_1$ to $C_4$ alkyl, which comprises the steps of (a) reacting a compound of the Formula (IX)

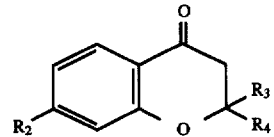

in a mixture of phosphorous trichloride oxide and dimethyl formamide to obtain a compound of the Formula (XI)

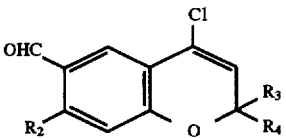

(b) dissolving the compound of the Formula (XI) in a carboxylic acid; and (c) boiling the dissolved compound of the Formula (XI) in the carboxylic acid in the presence of hydroxylamine hydrochloride and an alkali metal formiate.

15. A process for preparing a compound of the Formula (XV)

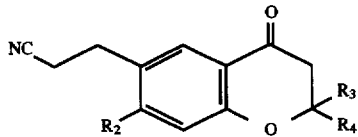

wherein

R₂ is $C_1$ to $C_4$ alkoxy; and

R₃ and R₄ are each $C_1$ to $C_4$ alkyl, which comprises the step of:

(a) condensing a compound of the Formula (XI)

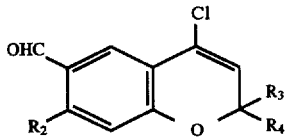

with acetonitrile in the presence of an alkali metal alcoholate to obtain a compound of the Formula (XIII)

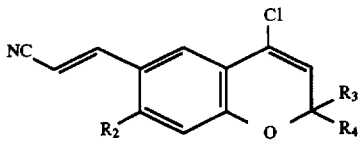

(b) reacting the compound of the Formula (XIII) with a mineral acid to yield a compound of the Formula (XIV)

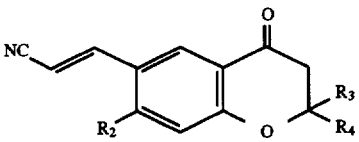

and;

(c) hydrogenating the compound of the Formula (XIV) in the presence of a catalyst under pressure.

16. A process for preparing a compound of the Formula (XVIII)

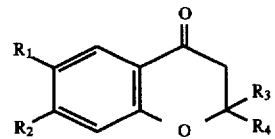

wherein

R₁ is hydrogen;

R₂ is hydroxy; and

R₃ and R₄ are each $C_2$ to $C_6$ alkyl, which comprises reacting the compound of the Formula (XVI)

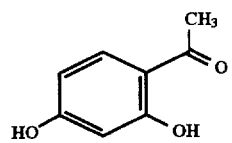

with a compound of the Formula (XVII)

in which R₃ and R₄ are each $C_2$ to $C_6$ alkyl.

17. The compound of the Formula (I) defined in claim 1 wherein R1 is cyano-$C_1$ to $C_6$ alkyl.

* * * * *